United States Patent
Beno et al.

(10) Patent No.: US 11,436,368 B2
(45) Date of Patent: Sep. 6, 2022

(54) PERSONAL DATA MANAGEMENT SYSTEM

(71) Applicant: Accenture Global Solutions Limited, Dublin (IE)

(72) Inventors: Tal Beno, Thornhill (CA); Yuly Basovich, Maple (CA); Andrew Xia, Toronto (CA)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/837,746

(22) Filed: Apr. 1, 2020

(65) Prior Publication Data
US 2020/0320220 A1 Oct. 8, 2020

Related U.S. Application Data

(60) Provisional application No. 62/829,363, filed on Apr. 4, 2019.

(51) Int. Cl.
*H04L 29/06* (2006.01)
*G06F 21/62* (2013.01)
(Continued)

(52) U.S. Cl.
CPC ...... *G06F 21/6245* (2013.01); *G06F 16/2379* (2019.01); *G06F 16/27* (2019.01);
(Continued)

(58) Field of Classification Search
CPC .. G06F 21/6245; G06F 16/27; G06F 16/2379; G06F 21/604; G06F 2221/2141; G16H 10/60; H04L 9/3247; H04L 2209/38
See application file for complete search history.

(56) References Cited

U.S. PATENT DOCUMENTS 10,291,395 B1 5/2019 Nenov et al.
10,417,219 B1 * 9/2019 Yang .................... H04L 9/0643
(Continued)

FOREIGN PATENT DOCUMENTS

KR 20200020122 A 2/2020

OTHER PUBLICATIONS

European Patent Office, Communication, Extended European Search Report issued for European Application No. 20191925.5, dated Feb. 4, 2021, 9 pages.

(Continued)

*Primary Examiner* — Shin-Hon (Eric) Chen
(74) *Attorney, Agent, or Firm* — Norton Rose Fulbright US LLP

(57) ABSTRACT

This disclosure relates to a system for managing personal data over a blockchain network. In an implementation, the system includes a user access provider (UAP) node in communication with a service provider (SP) node. The SP node may include an SP blockchain storing personal data on a SP transaction chain. The UAP node may store meta data of the user on a UAP transaction chain. The meta data may include access control information for the service provider to access the personal data. The UAP node may receive, from the SP node, an access request for the service provider to access a portion of the personal data of the user. The UAP node may access control information for the service provider based on the access request, update the meta data with the configured access control information, and replicate the meta data to the SP node via a blockchain transaction.

19 Claims, 10 Drawing Sheets

(51) Int. Cl.
  *G06F 21/60* (2013.01)
  *H04L 9/32* (2006.01)
  *G06F 16/27* (2019.01)
  *G16H 10/60* (2018.01)
  *G06F 16/23* (2019.01)

(52) U.S. Cl.
  CPC ........... *G06F 21/604* (2013.01); *G16H 10/60* (2018.01); *H04L 9/3247* (2013.01); *G06F 2221/2141* (2013.01); *H04L 2209/38* (2013.01)

(56) References Cited

U.S. PATENT DOCUMENTS

| | | | |
|---|---|---|---|
| 2017/0140375 A1 | 5/2017 | Kunstel | |
| 2017/0300898 A1 | 10/2017 | Campero et al. | |
| 2018/0032383 A1 | 2/2018 | Surcouf et al. | |
| 2018/0082024 A1 | 3/2018 | Curbera et al. | |
| 2018/0248880 A1 | 8/2018 | Sardesai et al. | |
| 2018/0294966 A1* | 10/2018 | Hyun | H04L 9/3226 |
| 2019/0028277 A1 | 1/2019 | Jayachandran et al. | |
| 2019/0205563 A1* | 7/2019 | Gonzales, Jr. | H04L 9/0637 |
| 2020/0160455 A1* | 5/2020 | Singh | H04L 9/3239 |
| 2020/0195647 A1* | 6/2020 | Sun | H04L 63/0807 |
| 2021/0135855 A1* | 5/2021 | Sunkavally | H04L 9/0822 |

OTHER PUBLICATIONS

Ølnes, S. et al., "Blockchain in government: Benefits and implications of distributed ledger technology for information sharing," Government Information Quarterly, 2017, Elsevier Inc., pp. 355-364, 10 pages.

Sunil Suseelan, Corda—A Blockchain Framework with No Chain of Blocks, Xoriant Blog, Oct. 9, 2019, Digital (https://www.xoriant.com/blog/digital/corda-blockchain-framework-no-chain-blocks.html), 9 pages, downloaded Mar. 20, 2020.

Corda Top Ten Facts #7: Both a blockchain and not a blockchain, Published Sep. 6, 2018, downloaded Mar. 20, 2020, https://www.corda.net/blog/corda-top-ten-facts-7-both-a-blockchain-and-not-a-blockchain/, 3 pages.

Corda Documentation, Key Concepts, https://docs.corda.net/docs/corda-os.4.4/key-concepts-transactions.html, Corda OS 4.4, 8 pages, downloaded Mar. 20, 2020.

Corda Documentation, States, https://docs.corda.net/docs/corda-os/4.4/key-concepts-states.html, Corda OS 4.4, 4 pages, downloaded Mar. 20, 2020.

HyperLedger Fabric, Ledger, https://hyperledger-fabric.readthedocs.io/en/release-1.4/ledger/ledger.html, 14 pages, downloaded Mar. 20, 2020.

* cited by examiner

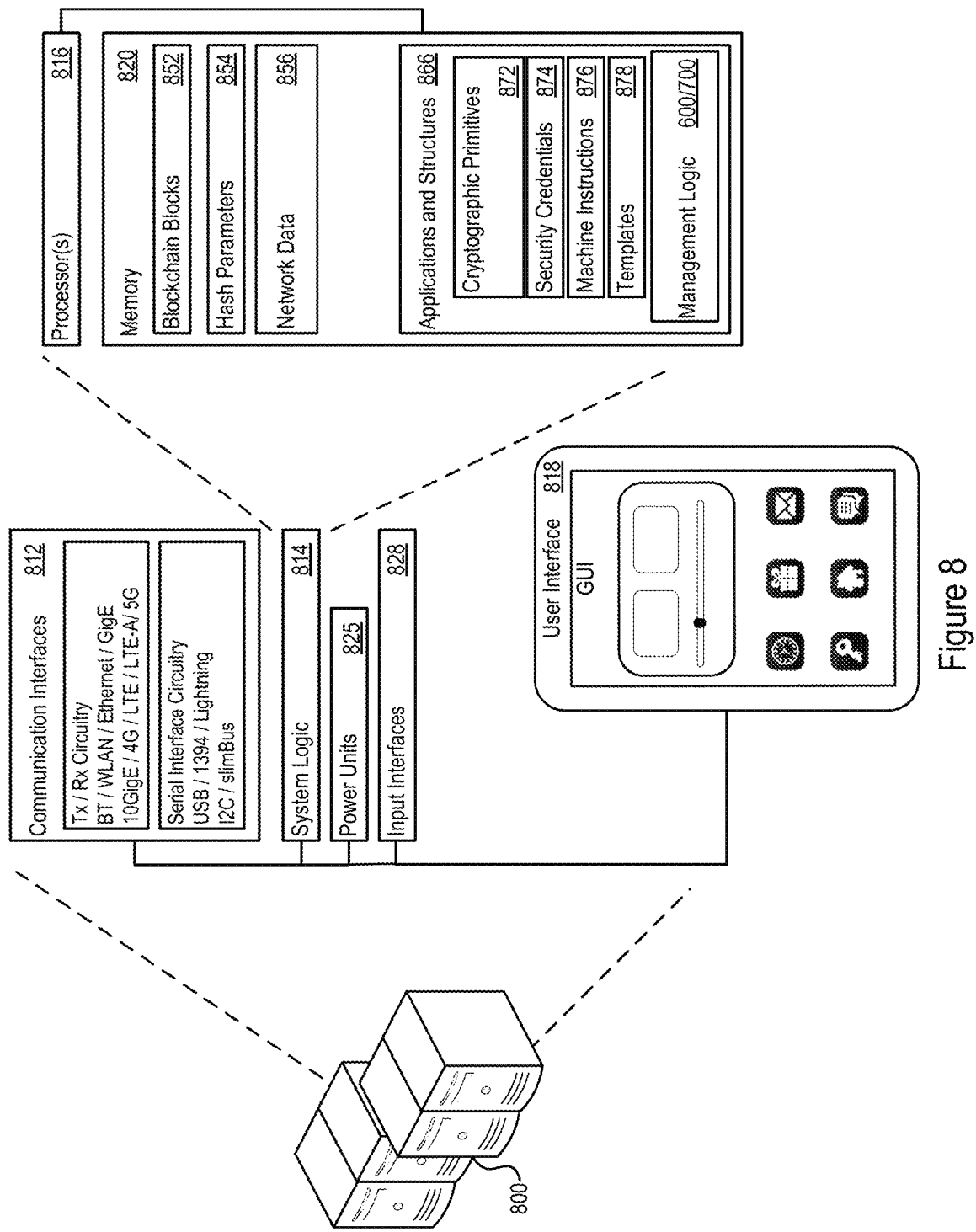

PERSONAL DATA MANAGEMENT SYSTEM

PRIORITY

This application claims priority to U.S. Provisional Patent Application Ser. No. 62/829,363, filed Apr. 4, 2019, titled System And Method For Managing Personal Data, which is incorporated by reference in its entirety.

TECHNICAL FIELD

This application generally relates to information management, and more particularly, to a personal data management system.

BACKGROUND

In the internet of various ecosystems such as a medical ecosystem, financial ecosystem, professional ecosystem, and social media ecosystem, companies and institutions, such as clinics, hospitals, pharmacies, diagnostic services, insurance, and/or online social media sites, act as service providers within the ecosystems. These service providers access and manage a user's personal data such as healthcare information, insurance information, and social contact information. However, these ecosystems provide the user with weak control over access and usage of their personal data by service providers. For example, the user typically has to hand over their personal data to the service providers in exchange for offered services.

BRIEF DESCRIPTION OF THE DRAWINGS

FIG. 8 illustrate an example specific execution environment for a system to implement aspects of the present disclosure.

DETAILED DESCRIPTION

Figure 1A:
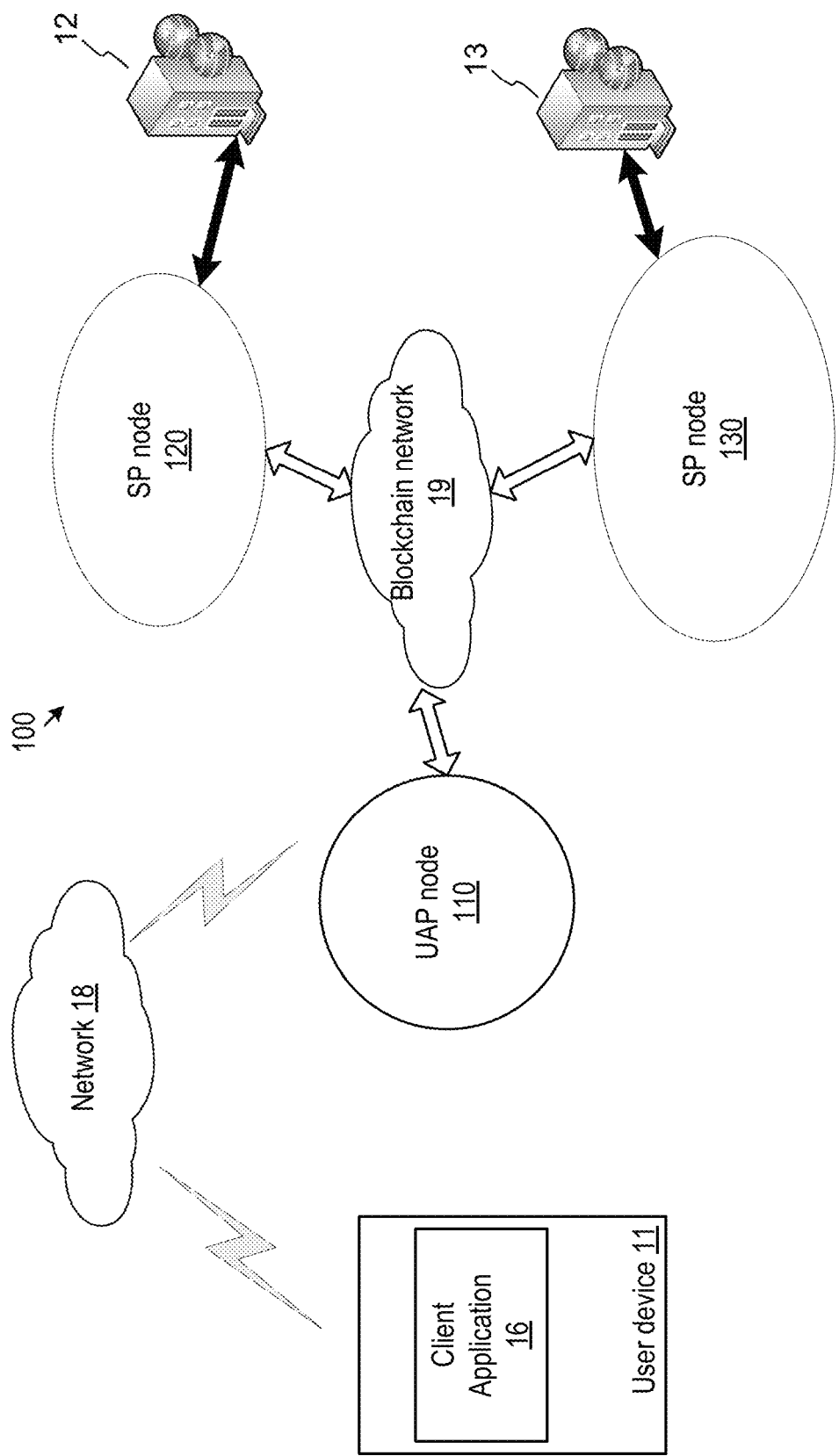
FIGS. 1A-1B illustrate a system for managing user personal data.

In traditional user personal data management approaches, service providers are managing personal data of a user in a secured permissioned network, though the user has no control over what is managed by the service providers. By contrast, the personal data management system described herein is established over a secured permissioned blockchain network in which service providers may manage a user's personal data under the supervision and control by the user. Thus, the user may control which service providers have access to the user's personal data and the user can terminate a service provider's access to his/her personal data at any time and/or for a reason of the user's choosing.

In traditional personal data management approaches, each service provider manages personal data on its own, and the industry lacks collaboration between service providers. This can cause the user to lose sight and/or governance over where the user has left their personal data. These approaches may also lead to inconsistent and/or fragmented information spreading across many service providers. For example, when a user updates their personal data with one service provider, it is not synchronized with the other service providers.

By contrast, the personal data management system described herein promotes an enterprise level collaboration where updating information in one service provider, by or on behalf of a user, may synchronize and pass the updated information to other enabled service providers, for example, via blockchain transactions. Moreover, the system enables a user to know exactly which service provider(s) the user has left their personal data with.

In traditional personal data management approaches, personal data is managed off-ledger. In other words, personal data of users/customers is not stored in a blockchain, and thus is actually "owned" by the respective service providers. Data exchange between service providers is typically done peer-to-peer and is unidirectional. Moreover, data is typically exchanged once when a user initializes services with a source service provider and may not be kept up-to-date unless the user manually pushes an update of the data to the source service provider. In the personal data management system described herein, the personal data is managed via blockchain transactions, where data is synchronized transparently between permissioned service providers, and/or symmetrically across multiple service providers to provide ongoing personal data updates over time.

One of the challenges in managing personal data on blockchain is the need to comply with government mandated privacy requirements, such as, but not limited to, General Data Protection Regulation (GDPR) requirements. Under the GDPR, a user may (among other things) request to purge the his/her personal data. The removal of data within a blockchain runs counter to the integrity and immutability of blockchain, which are key value attributes of blockchain use. The personal data management system described herein may be used in compliance with GDPR and without violating immutability aspects of blockchain by storing each user's personal data to a separate and independent part of a blockchain. In this way, when a user desires to purge their personal data from a service provider, the system may simply discard the part belonging just to that user in the blockchain, without the purging tampering with the integrity/security of the remainder of the blockchain.

To enable a user control over with whom their personal data is shared, the personal data management described herein ensures that the user will not be dependent on service providers to purge the personal data. In this regard, a novel blockchain network node is introduced, which is referred to as a "User Access Provider" (UAP) node. A user may get an identity through the UAP node as well as manage access permissions with service providers. The user can revoke access to their personal data for specific service providers directly through the UAP node and thus bypass specific service providers in terms of providers controlling use of the user's data.

The UAP node operates on behalf of the user to represent the user's interests regarding his/her personal data. The UAP node has no access to the personal data and its primary role is to represent the user's interests. The UAP node may not only assist a user with managing personal data being provided to service providers, but also enforces the user's desire to remove data from a service provider and/or the network. The blockchain infrastructure may help enforce compliance consensus mechanisms, which ensure all nodes agree on which transactions are legitimate and are added to the blockchain.

In some implementations, data may be signed by a user and verified by a service provider. The user's signature represents a consent for the service provider to access and/or manage the user's personal data For example, data may be signed prior to placing it on the blockchain. In addition or alternatively, a user may give such consent in other ways.

In this way, unlike the traditional management system which does not allow for consistent data management, the personal data management system described herein allows a user to manage data consistently across all service providers. The personal data management system described herein enables a user's personal data to be synchronized across multiple service providers. The user may make a single update and it can be pushed to multiple service providers. Service providers may always have current user personal data and up-to-date use permissions. Additionally, in the personal data management system described herein, a user may digitally sign any update made to personal data. This may increase the security of the system and reduce the possibility of abuse by external parties as well as by the service providers.

Herein, a user may be a natural person who may utilize service providers to provide services such as financial services, healthcare services, social media services, insurance services, and the like. By providing such services, the respective service providers may have access to and may manage different kinds of corresponding personal data such as financial data, healthcare data, social contact data, insurance data and other information specific to the user that is not publically available. Service providers are not limited to the above examples and may represent any entity providing one or more services which relate to or use one or more kinds of the user's personal data.

FIG. 1A illustrates an example of a personal data management system 100 for managing personal data of a user over a network 18 and a blockchain network 19. Instead of a blockchain, such as a Hyperledger Fabric where changes are stored as batches of changes (grouping transactions) forming the blocks, the system 100 may store changes as a sequence of states forming a transaction in order to manage a separate ledger table per user/functional layer. Examples of such state based blockchain functionality include R3 Corda and Oracle Blockchain Tables. The system 100 may provide distribution and synchronization of a user's personal data and meta data.

In the system 100, a state may be an immutable object representing a fact known by one or more network nodes at a specific point in time. Herein, states may contain a user's personal data or meta data. States are evolved by marking the current state as historic and creating an updated state, which forms a sequence of states called a state chain. Each state chain is separate in the blockchain. Transactions may represent a single link in the state sequences. The transactions associated to a same sequence of states may form a transaction chain. Each transaction chain is separate in the blockchain. Both state chains and transactions chains are contained in a blockchain of an individual node.

Within the system 100, only parties involved in a blockchain transaction and those who need to assure themselves of the transaction's provenance may have access to the details of the transaction. Thus, two or more participants may transact with one another, sharing only necessary information between them. The blockchain transaction may be confirmed through a consensus mechanism using a variety of algorithms, including, for example, Byzantine Fault Tolerant algorithms. The consensus mechanism is used to confirm the involved parties are synchronized with each other and agree on which transactions are legitimate and are added to the transaction chain. Additionally, a transaction may be in a cryptographically linked (chained) chain to the transactions it depends on and not to some other set of transactions. Thus, storage and verification does not rely on a chain of blocks like other blockchain frameworks, such as Hyperledger Fabric, which bundles up a set of transactions into a block.

Data associated with a user may include the user's personal data and the user's meta data. Personal data (also referred to as user personal data or personal information) may include information which is related to one or more of: identified natural persons; personally identifiable information of natural persons; personally identifying information of natural persons; user specific information of natural persons that is or should be under the control of the user and otherwise not publically available; or some combination thereof. For example, personal data may include data identifying a user such as a social security number, a driver license number, an employee identifier, data identifying characteristics about the user, data identifying the health status of the user, and the like.

Personal data may include multiple data records, which may be categorized into different data types. The data types may be organized in a manner that facilitates customized access control for different types of data records as well as personal data synchronization/replication between the network nodes. A user's meta data may include, for example, access control information to access the user's personal data, a user identifier of the user, and other information assisting to control access to the user's personal data. The access control information may include, for example, a create permission, a read permission, an update permission, and/or a delete permission.

In the example of FIG. 1A, the system 100 includes a UAP node 110 and service provider (SP) nodes 120/130. The UAP node 110 may operate on behalf of a user while the SP nodes 120/130 may operate on behalf of respective service providers. The UAP node 110 and the SP nodes 120/130 may communicate via the blockchain network 19. The blockchain network 19 may facilitate data replication or synchronization between the UAP node 110 and the SP nodes 120/130 via a blockchain transaction. The blockchain transaction may be requested by the UAP node 110 or the SP nodes 120/130 to include, for example, the user's personal data or the user's meta data. Instead of broadcasting the requested transaction in the blockchain network 19, the requested transaction may be communicated between the nodes relevant to the transaction. The relevant nodes may validate the transaction against, for example, preconfigured validation rules. The validated transaction may update the personal data or user data to corresponding state chain and be appended to a corresponding transaction chain in a blockchain of the individual nodes.

The network 18 may include the Internet, wireless or wireline networks, other LAN/WAN networks whether private or public, or any other communication network capable of transmitting, receiving, or transporting data. Example hardware within the network 18 may include server computers, communication satellites, computer systems, computer devices, network devices (such as switches, routers, and hubs), databases, mobile devices connected, e.g., through cellular base stations, and the like. The blockchain network 19 may be included as part of the network 18 or may be a separate communication network.

In the system 100, a user's personal data and the user's meta data may be managed separately. For example, the UAP node 110 may have access to a user's meta data but may not have access to personal data of the user. Techniques for preventing access to personal data by the UAP 110 include not providing the UAP node 110 with an address or pointer to the data location of the personal data, and other relevant techniques. Lack of access to the user's personal data enables the UAP node 110 to act on behalf of the user with authorization to manage the user's meta data. Managing user meta data may include, for example, meta data creation, modification, deletion, etc. User device 11 may communicate with the UAP node 110 in behalf of a user. For example, a client application 16 of the user device 11 may communicate with the UAP node 110 via the network 18. The client application 16 may include a graphical user interface (GUI) for receipt of the user's input. The user device 11 may include but is not limited to a mobile phone, smartphone, tablet, laptop computer, computer, or other device(s) capable of communicating over a network.

Figure 1B:
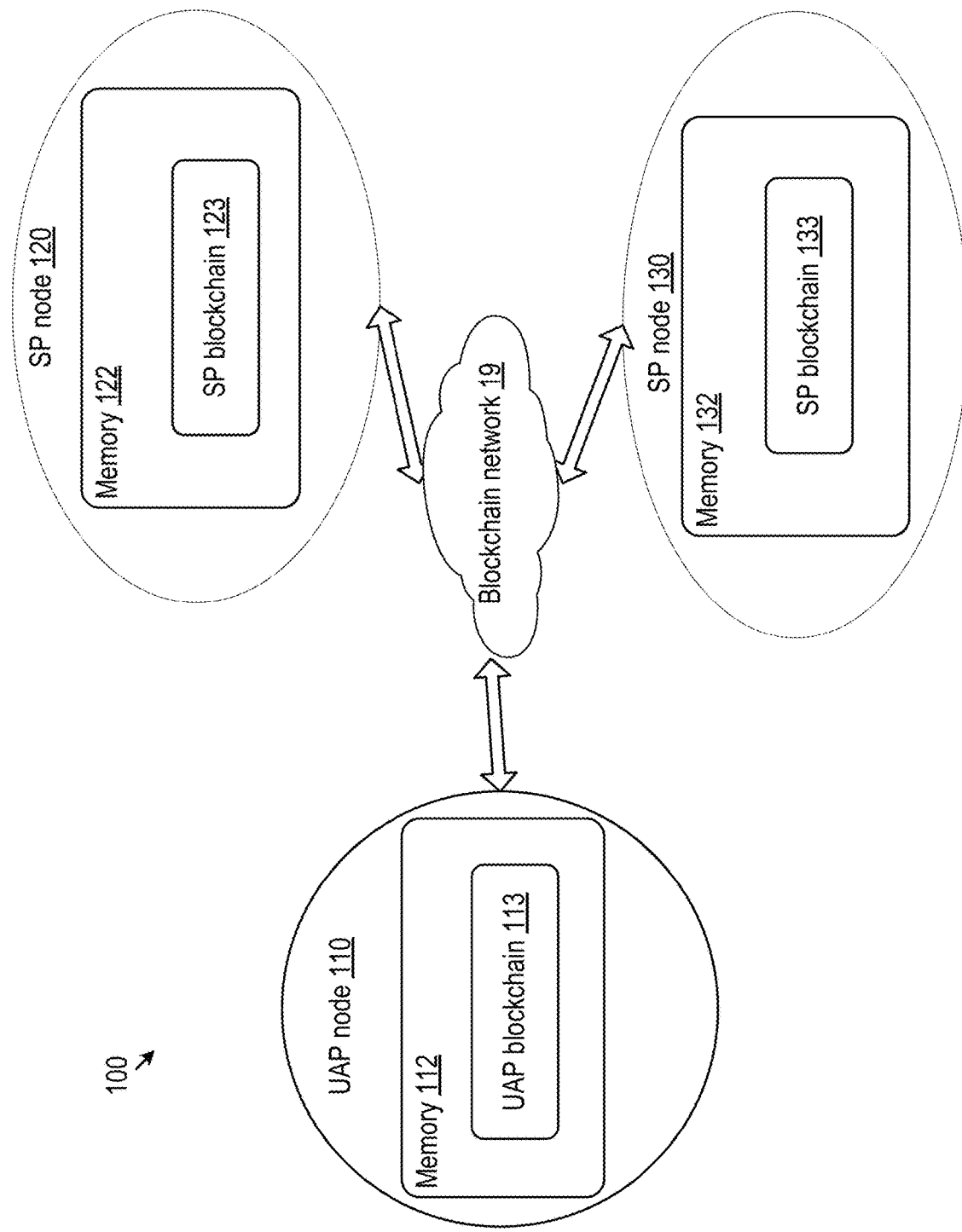

With reference to FIG. 1B, in an implementation, a user's meta data may be stored in the UAP blockchain 113, which may be stored on memory 112 of the UAP node 110. The SP nodes 120/130 may store a user's personal data on behalf of the corresponding service providers 12/13. Each of the service providers 12/13 may operate the SP nodes 120/130 and manage the user's personal data via the SP node 120/130 within the system 100. The SP nodes 120/130 may store a user's meta data but have no right to modify the meta data stored on SP node 120/130. The service providers 12/13 may enforce access permission compliance as a responsibility of being custodian of each of the user's data. The service providers 12/13 may store data locally to ensure quality of service and compliance to regulations. Thus, the SP nodes 120/130 may be respectively located at local sites of service providers 12/13 serving the user. Alternatively, or in addition, the SP nodes 120/130 may be located at remote sites away from the service providers 12/13 and accessible over the networks 18 and 19.

Figure 1C:
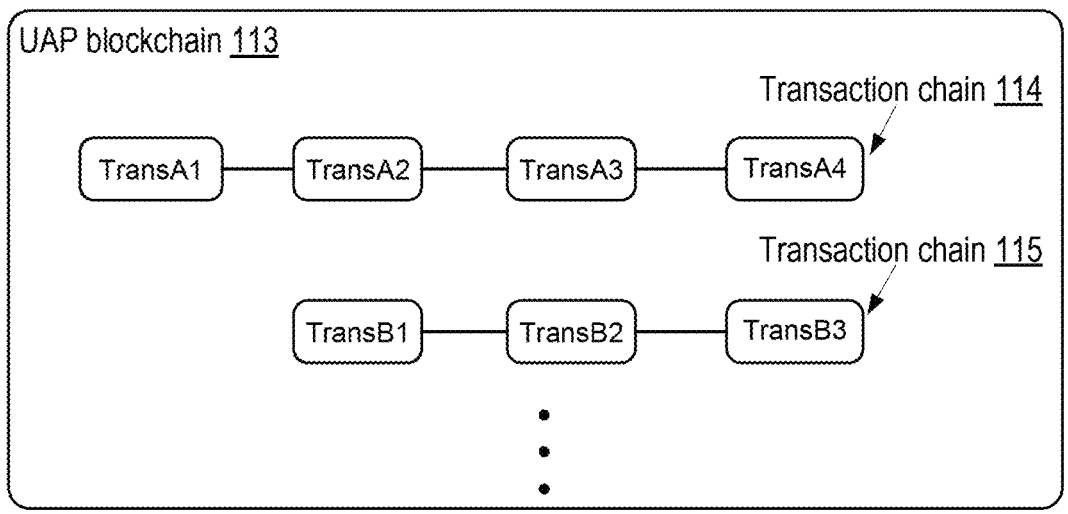
FIG. 1C illustrates an example data structure of a user access provider blockchain.

FIG. 1C shows an exemplary data structure of the UAP blockchain 113. The UAP blockchain 113 may include a plurality of separate transaction chains, each of which may include transactions of respective users' meta data. In other words, transaction chains for meta data of different users are not linked with each other. For example, the transaction chain 114 of the UAP blockchain 113 may store transactions of a first user's meta data while the transaction chain 115 of UAP blockchain 113 may store transactions of another (e.g., a second) user's meta data. Further, the UAP blockchain 113 may include a plurality of separate state chains, each of which may include historic states and a current state of respective users' meta data. The state may represent a snapshot of a user's meta data.

Figure 1D:
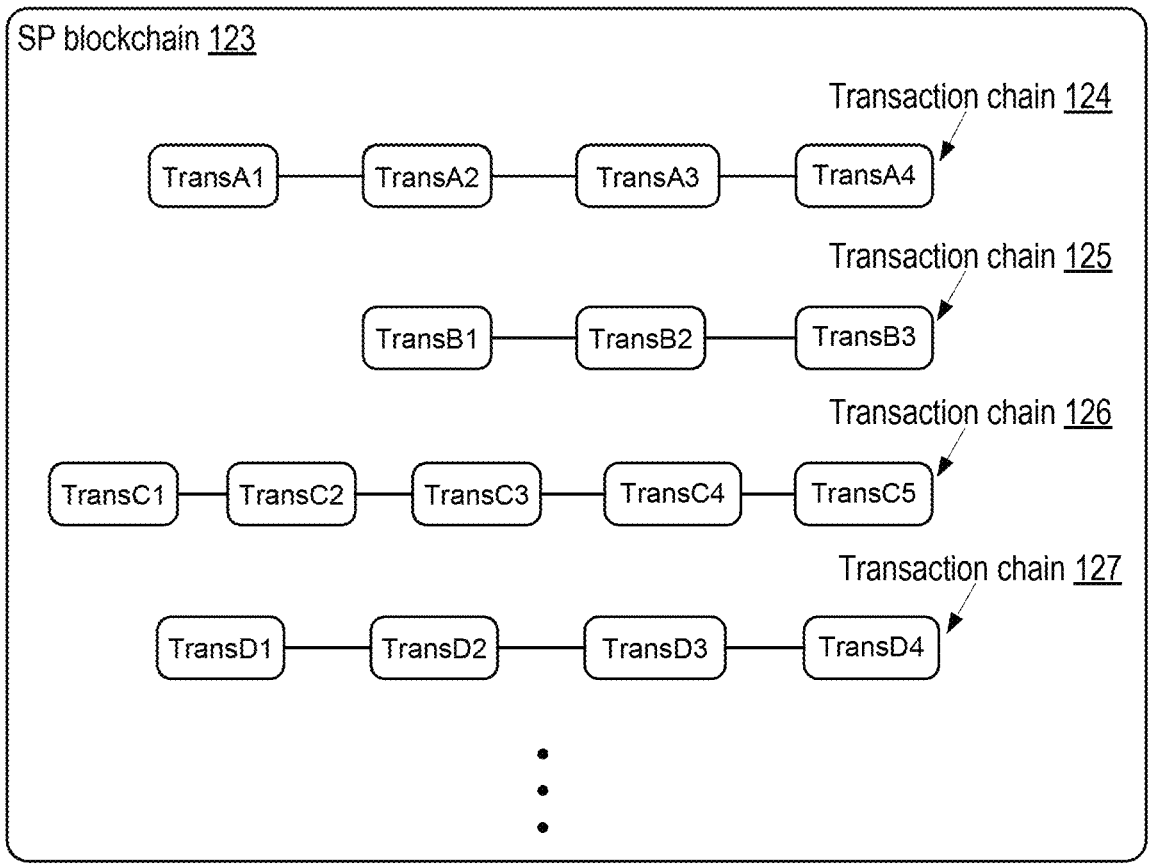
FIG. 1D illustrates an example data structure of a service provider blockchain.

With regards to SP nodes, the SP node 120 may have a memory 122 storing a SP blockchain 123 and the SP node 130 may have a memory 132 storing a SP blockchain 133. Take the SP blockchain 123 as example, the SP blockchain 123 may store at least a portion of the user's meta data and at least a portion of the user's personal data. FIG. 1D shows an exemplary data structure of the SP blockchain 123. Similar to the UAP blockchain 113, the SP blockchain 123 may include a plurality of separate transaction chains, each of which may include transactions of a respective user's meta data. For example, the transaction chain 124 may store transactions of a user's meta data while the transaction chain 125 may store transactions of another user's meta data.

Further, the SP blockchain 123 may include a plurality of additional separate transaction chains, each of which may include transactions of respective users' personal data. For example, the transaction chain 126 of the SP blockchain 123 may store transactions of a user's personal data while the transaction chain 127 of the SP blockchain 123 may store transactions of another user's personal data. Moreover, the SP blockchain 123 may include a plurality of separate state chains (not shown), each of which may include historic states and a current state of respective users' personal data. The state may represent a snapshot of a user's personal data.

The UAP node 110 may replicate or synchronize at least a portion of the meta data to the SP nodes 120/130 and stored, for example, on the SP blockchains 123/133. The replication and synchronization among the blockchains 113, 123 and 133 may be achieved through blockchain transactions.

For simplicity and clarity, only one UAP node 110 and two SP nodes 120/130 are shown in the example system 100 illustrated in FIG. 1B. It will be appreciated that multiple UAP nodes and SP nodes may be included in the system 100. For example, one or more UAP nodes may act on behalf of one or more different users to manage their meta data.

Figure 2:
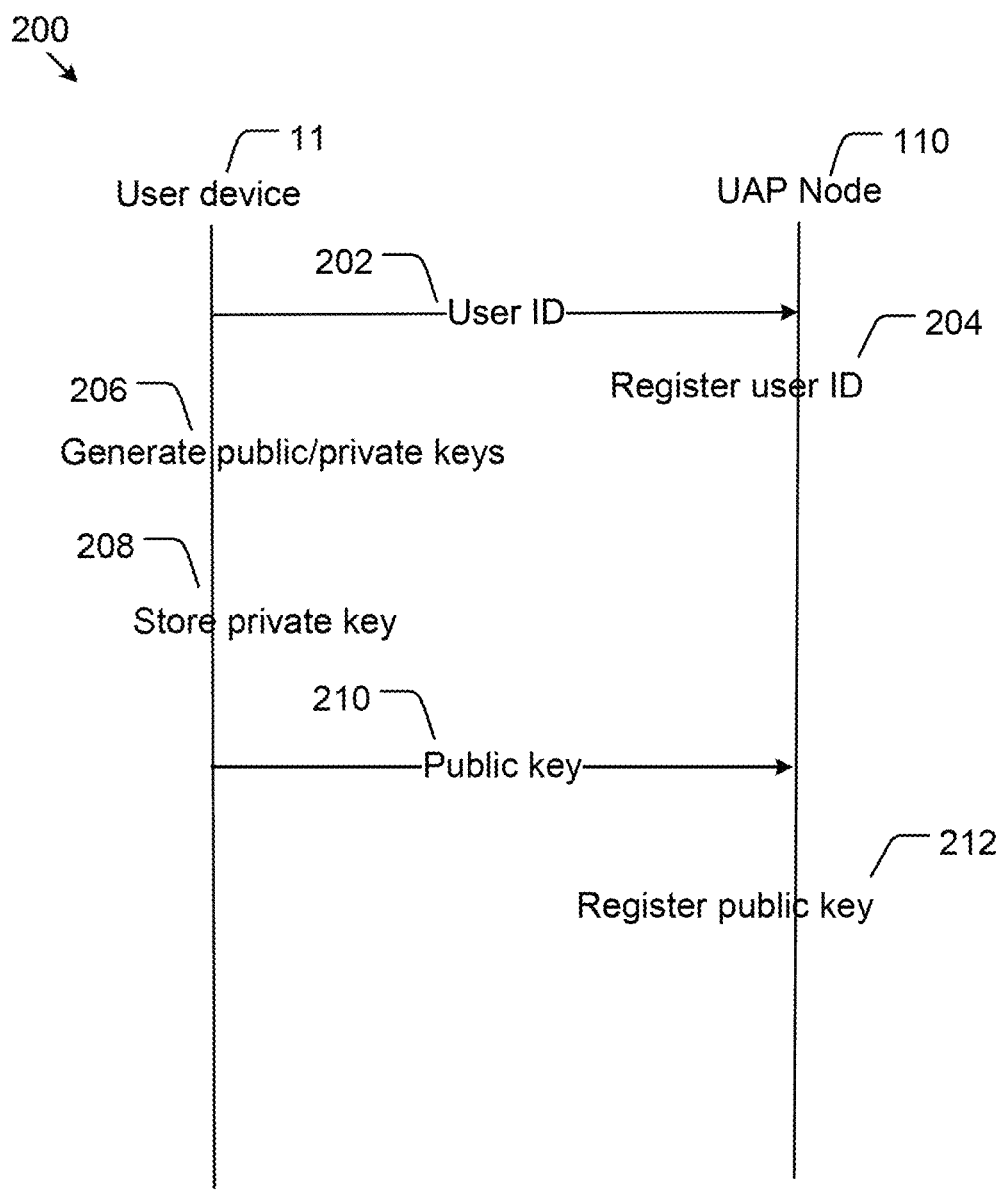
FIG. 2 illustrates an example interaction between a user device and a user access provider node.

FIG. 2 shows exemplary logic 200 for user device 11 to register with UAP node 110 on behalf of a user. The user device 11 may communicate with the UAP node 110 via a client application 16. The client application 16 may include a GUI for receiving a unique user identifier, such as user ID, biometric identifier (e.g., fingerprint, retina scan, facial scan, etc.) or other form of digital ID. The user device 11 may communicate a user registration request including the user ID as well as authentication information such as a password/secret to the UAP node 110 via the client application 16 (202). Alternatively or additionally, the authentication information may include, for example, biometric information such as fingerprint of the user. Upon receiving the user registration request, the UAP node 110 may register the user ID (204). For example, the UAP node 110 may generate meta data for the user and add the user ID to the meta data. In another implementation, the UAP node 110 may generate the user ID and return the generated ID to the user device 11 in response to the registration request.

In this way, the user device 11 may login and access the UAP node 110 to configure access control information for service providers interacting with the user device 11 to provide requested services to a user of the user device 11.

In an implementation, the user device 11 may generate a pair of public/private keys for the user, for example, using the client application 16 (206). The pair of public/private keys may work to secure and authenticate message. A public key can be shared with other devices. In contrast, a private key may belong to, and may remain private, only an owner. The owner can "sign" a message by combining the message with the private key to create a digital signature (also referred to as "signature") on the message. Anyone with the owner's corresponding public key can combine the same message and the digital signature associated with the message with the public key to verify whether the signature was valid, i.e. signed by the owner using the corresponding private key.

The client application 16 may store the private key locally on the user device 14 (208), and communicate the public key to the UAP node 110 via the network 18 (210). In another implementation, the public key may be communicated to the UAP node 110 as a part of the user registration request. The UAP node 110 may register the public key for the user (212), for example, by adding the public key to the meta data of the user stored on the transaction chain 114 of the UAP blockchain 113. As such, the data communication from the user device 11 to the UAP node 110 may be signed with the private key on the user side to ensure that the data communication comes from the user device 11.

Figure 3:
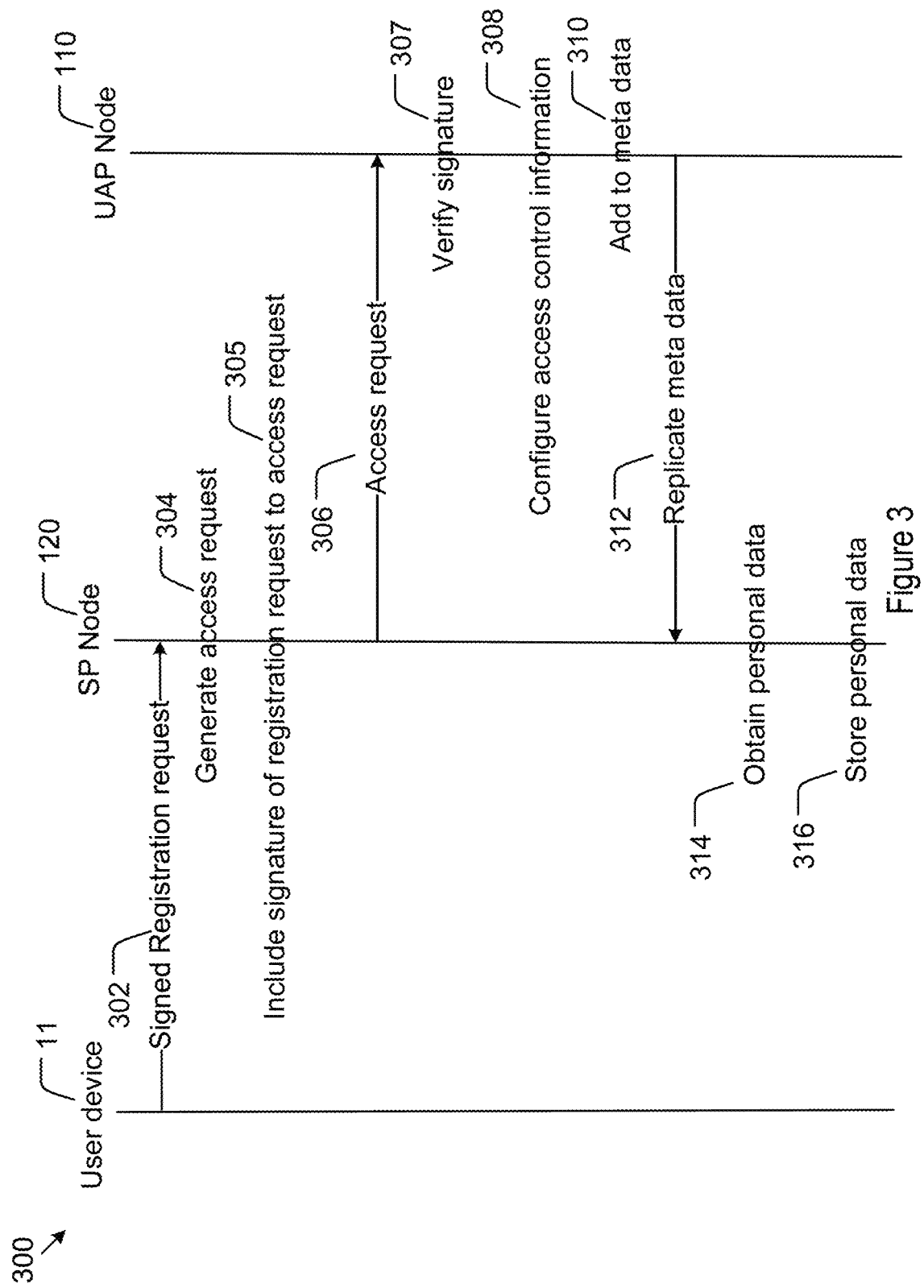
FIG. 3 illustrates an example interaction among a user device, a service provider node, and a user access provider node.

FIG. 3 shows exemplary logic 300 for user device 11 to register with a new service provider 12 over the network 18 and blockchain network 19 to obtain services of the service provider. The user device 11 may communicate a registration request to the SP node 120, for example, via the client application 16, to register the user device 11 with the service provider 12 (302). The registration request may, for example, include the user ID that the user device 11 has registered with the UAP node 11 and signed with the private key of the user. Upon receiving the registration request, the SP node 120 may generate an access request for the service provider 12 to access the personal data of the user based on the registration request (304) and include the user ID of the user and a signature of the registration request to the access request (305). The signature of the user registration request can be used to authenticate the source of the request. When ownership of the signature is bound to a specific user, an authentic signature shows that the registration request was sent by that user.

The SP node 120 may then communicate the access request to the UAP node 110 (306). For example, the SP node 120 may call an application program interface (API) of the UAP node 110 to request access to personal information of the user identified by the User ID. The UAP node 110 may verify the signature in the access request using the public key of the user (307). After determining that the signature is authentic, the UAP node 110 may configure access control information for the service provider 12 to access the personal data of the user based on the access request (308). In an implementation, the UAP node 110 may configure the access control information using access permission rules preconfigured and stored in the UAP node 110 by the user. For example, the UAP node 110 may grant the service provider 12 only read permission to the user's personal data. In another example, the UAP node 110 may grant the service provider 12 a create permission, a read permission, and an update permission.

In another implementation, the UAP node 110 may request the user device 11 to configure the access rights for the service provider 12 to access the personal data of the user. In response to the request, the user device 11 may access stored information, or receive inputs from the user device 11 to configure the access rights via the GUI of the client user application 16. The user device 11 may communicate the configured access rights to the UAP node 110. The UAP node 110 may receive and store the access rights as configured access control information for the service provider 12.

Optionally, the data records in the personal data of the user may be categorized into different data types. The data type may further include subcategorizations of content in the data records. For example, the personal data of the user device 11 may include a data type identifying healthcare records of a user of user device 11. The healthcare records may be subcategorized into sub data types of, for example, personally identifiable information (PII) type and medical data type. The PII type may be further sub-categorized into sub-sub datatypes such as, for example, a sensitive PII data type, a medical PII data type, and an ordinary PII data type. The medical data type may be subcategorized into sub-sub datatypes such as, for example, a prescription data type and a test report type.

The access request from the SP node 120 may further include data types of the data records that the service provider 12 requests to access. The UAP node 110 may configure the access control information differently for the service provider 12 for each data type to which the service provider 12 requests access. For example, where the service provider 12 is a hospital or 911 emergency service, which requests access to all data types of data records in the personal data of the user, the UAP node 110 may configure PII-type data records with read permission, but not create/update permissions, while configuring medical-data-type data records with read, create, and update permissions. Where the service provider 12 is a pharmacy and requests to access prescription-data-type data records and test-report-type data records, the UAP node 110 may configure prescription-data-type data records with read/create/update permission, but not provide create/update permissions while configuring test-report-type data records so that only read access is permitted.

Optionally or in addition, the UAP node 110 may configure a custom group access permission for a list of service providers where a specific data record is only accessible to a selection of a specified group of service providers. For example, the UAP node 110 may create a custom permission record on the transaction chain 114 of the UAP blockchain 113 for the specific data record listing the service providers in the group that can read and/or update that data record.

Still referring to FIG. 3, after configuring the access control information for the service provider 12, the UAP node 110 may update the meta data of the user with the access control information, for example, by adding the access control information to the meta data of the user (310), which may be stored on, for example, the transaction chain 114 of the UAP blockchain 113. Therefore, the meta data of the user may include the access control information for all service providers requesting to access the personal data of the user.

Subsequently, the UAP node 110 may replicate the updated meta data of the user to the SP node 120 via blockchain transactions, which may then be stored, for example, on the transaction chain 124 of the blockchain 123 (312). The UAP node 110 may further synchronize the updated meta data of the user to the SP nodes of other service providers that are providing services to the user device 11, via blockchain transactions.

In another implementation, the UAP node 110 may replicate a portion of the updated meta data of the user to the SP node 120. For example, the portion including the access control information for the service provider 12 to access the personal data of the user is replicated to the SP node 120.

Then, the SP node 120 may obtain the personal data of the user based on the meta data stored on the SP node 120 (314) and store the personal data of the user on the SP node 120 (316). For example, the SP node 120 may identify the data types to which access has been granted by access permission(s) included in the meta data. Among other SP nodes and corresponding service providers who are serving the user, the SP node 120 may select another SP node 130 that has access to same/similar data types as the SP node 120. As such, the SP node 120 may replicate the personal data of the user device 11 from the selected another SP node 130. The SP node 120 may replicate the data records in the personal data per data type via blockchain transactions. In other words, different data types of data records may be replicated in separate blockchain transactions. The SP node 120 may store the replicated personal data of the user on the transaction chain 126 of the SP blockchain 123.

As an example, both the service provider 12 and the service provider 13 are pharmacies, and thus may access the same data type of data records, i.e., prescription data type. When the service provider 13 is already serving the user device 11, and the SP node 120 is obtaining personal data of the user to begin serving the user, the SP node 120 may select to replicate, per the prescription data type, the personal data of the user from the SP node 130 of the service provider 13 already providing service to the user. Optionally, or in addition, the system 100 may use a custodian SP node, which may be not associated with any other service provider and may function to backup personal data of the user across the system 100. For example, the custodian SP node may backup the personal data of the user in a blockchain, which may be stored in a memory on the custodian SP node.

The system may include ecosystems for the data types. As used herein, ecosystem may describe the different data types of data records included in the personal data managed on the SP nodes for users. A user may have multiple service providers who access/manage his/her personal data. Each data type of data records distributed across the SP nodes is referred to as its own ecosystem. Service providers can participate in many ecosystems, and thus manage different data types of data records on the SP nodes. As an example, the personal data of a user may include healthcare data records which are categorized into three data types: allergy, prescription, and vaccination. Accordingly, there are three corresponding ecosystems, namely, an allergy ecosystem, a prescription ecosystem, and a vaccination ecosystem. A service provider 12 may participate in, for example, the allergy ecosystem and the prescription ecosystem so as to manage the allergy data records and the prescription data records on its SP node 120.

The custodian SP node may have no write permission to personal data of a user. Rather, it may be used to replicate/synchronize personal data of a user to other SP nodes or other type of storage device, such as a local digital wallet of the user. As such, where the SP node 120 fails to find a proper SP node to replicate the personal data of a user device 11, the SP node 120 may replicate personal data from the custodian SP node. The replicated data may be the data records of the user in the ecosystems that the service provider 12 participates in. In other words, the SP node 120 may replicate the personal data of the user per data type that the service provider 12 may access or manage via blockchain transactions, as authorized by the user.

Figure 4:
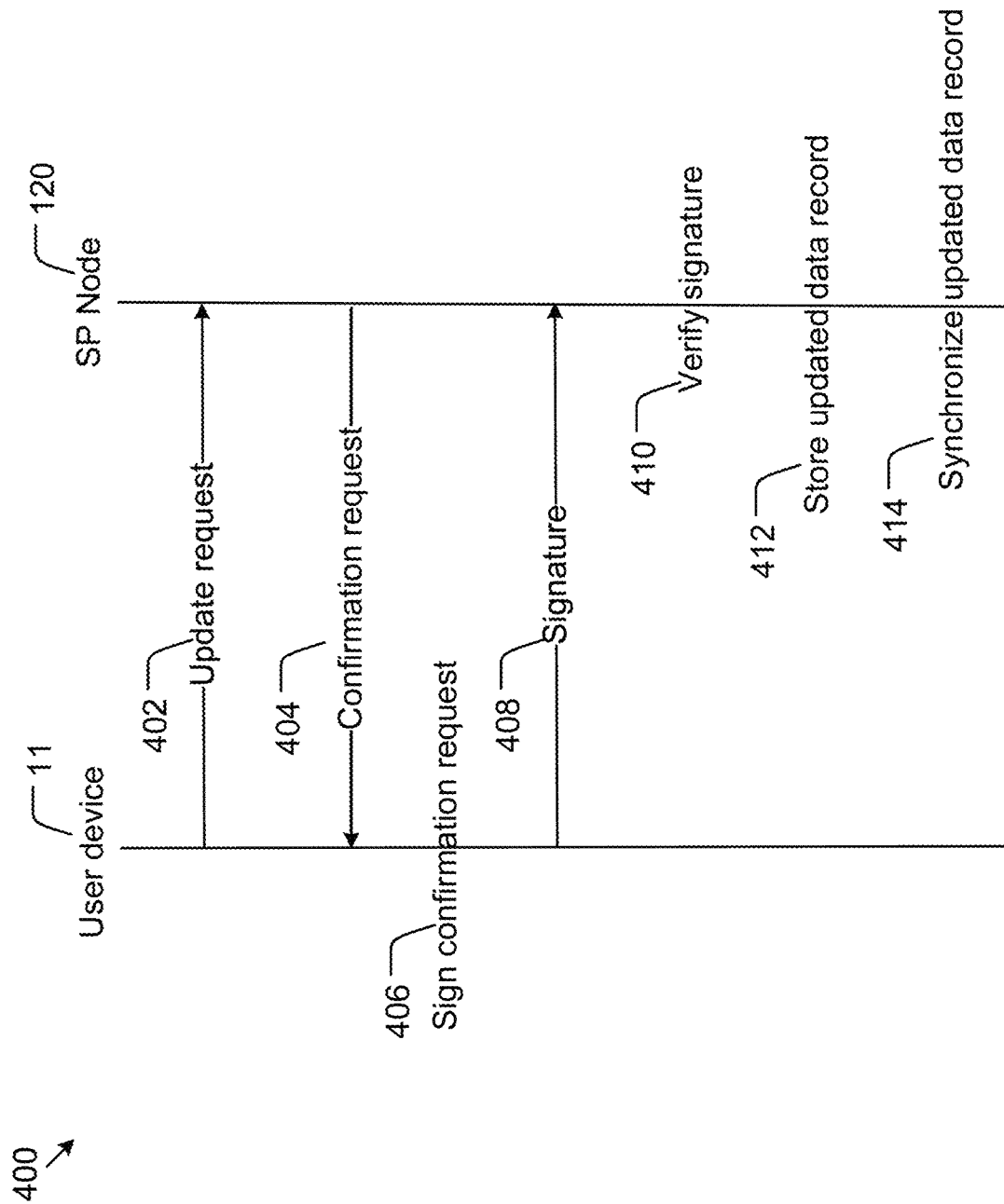
FIG. 4 illustrates an example interaction between a user device and a service provider node.

FIG. 4 shows an exemplary logic 400 for the service provider 12 to update the personal data of the user over the blockchain network 19. When the user device 11 creates/updates personal data of the user, the user device 11 may communicate an update request to the SP node 120, for example, via the client application 16 (402). The update request may be a request, for example, to update a vaccine-type data record in the personal data of the user device 11.

Upon receiving the update request, the SP node 120 may communicate a confirmation request to the user device 11 via the client application 16 (404). Based on the confirmation request, the client application 16 may generate a prompt to a user of the user device 11 to confirm the data record update. The user device 11 may receive, via a user interface, confirmation by a user to "sign" the confirmation request with the private key of the user to generate a digital signature of the confirmation request (406). The digital signature of the confirmation request may be communicated to the SP node 120 via networks 18 and 19 by the client application 16 (408). After receiving the signature, the SP node 120 may leverage the public key of the user stored on the SP node 120 to verify the signature (410). When determining that the signature is authentic, the SP node 120 may store the updated data record, for example, on the transaction chain 126 of the SP blockchain 123 (412). Such digital signature mechanism may ensure that data records can be updated to the personal data stored on the SP node only when the update is confirmed by the user device 11. This may increase the security of the system and reduce the possibility of abuse by external parties as well as by the service providers.

Optionally, prior to communicating a confirmation request to the user device 11 (404), the SP node 120 may determine if a digital signature of the user is required in order to update the data record. It may be that the user's signature is required in order to update or otherwise manage data records belonging to some data types (or sub-data types), but not required in managing data records belonging to other data types (or sub-data types). Data types that require signatures and data types not requiring signatures may be preconfigured, for example, by user device 11. If a data type is indicated as not requiring signature, the service provider 12 may manage the user's data records of the data type without the user's confirmation. To the extent that the multiple data types do not require a user's signature, the personal data of the user in those data types is solely managed by the service provider.

If the SP node 120 determines that the data type of the updated data record does not require a user's signature, the SP node 120 may store the updated data record in the blockchain without communicating a confirmation request to the user device 11.

The SP node 120 may synchronize the updated data record to blockchains stored on other SP nodes of the system 100 having access to data records of the user belonging to the same data type with the updated data record (414). For example, where the data type of the updated data record is a vaccine type and the SP node 130 has access to the vaccine-type data records of the user, the updated data record may be synchronized to the SP node 130 and stored, for example, in the SP blockchain 133 on the SP node 130 via a blockchain transaction. As such, the user's personal data may be synchronized transparently between permissioned service providers via blockchain transactions. The user only has to make a single update and it can be pushed to multiple service providers. This may provide a continuous data update over time across the permissioned service providers and the personal data may be managed consistently across all service providers.

Figure 5:
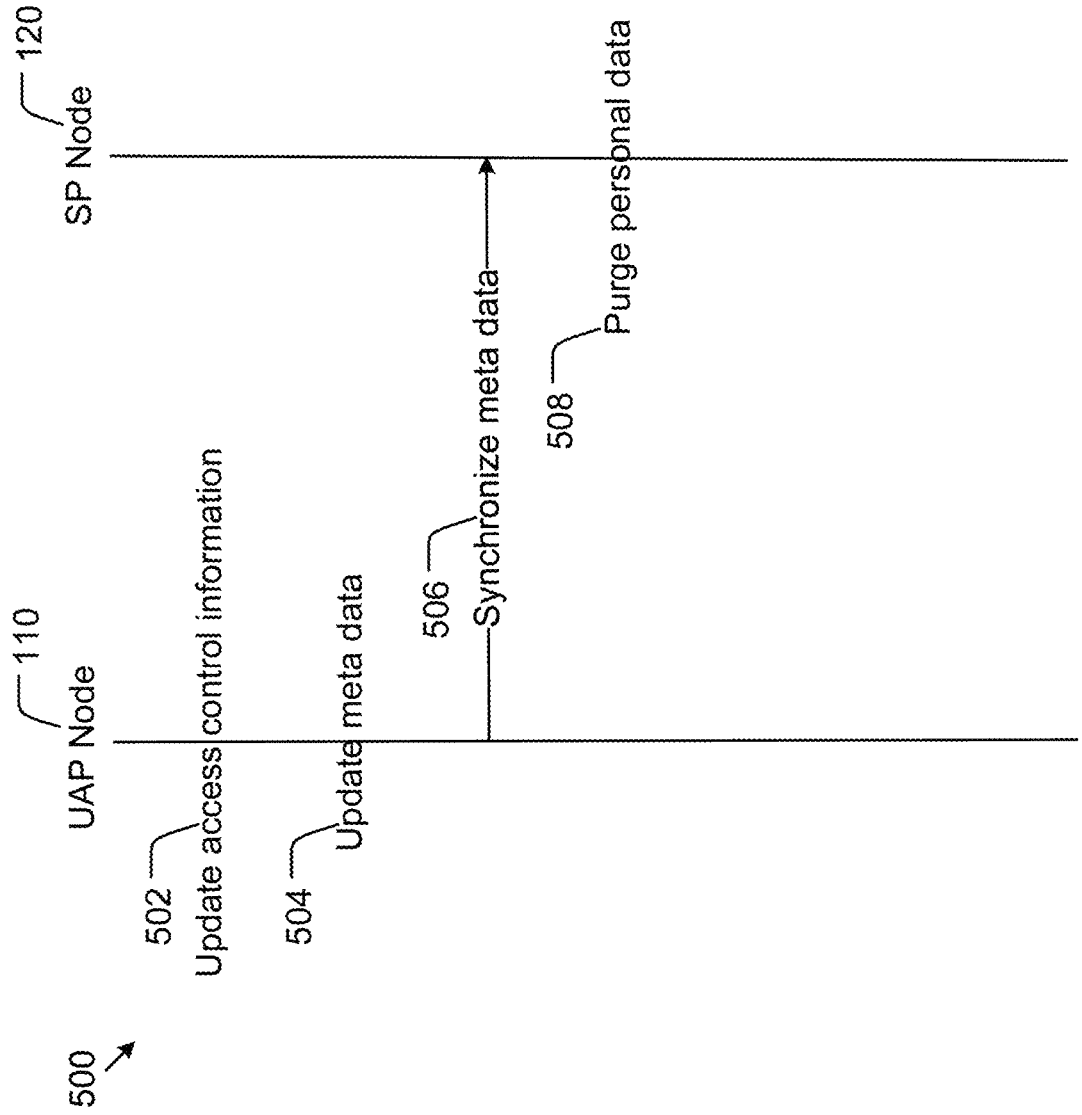
FIG. 5 illustrates an example interaction between a user access provider node and a service provider node.

FIG. 5 shows an exemplary logic 500 for revocation of access of a service provider 12 to the personal data of a user over the blockchain network 19.

Referring to FIGS. 1A, 1B and 5, where the user via the user device 11 revokes access of the service provider 12 to the personal data of the user, the data may be purged from the SP node 120. This can be achieved by the service provider 12 deleting the personal data. Alternatively, the personal data of the user may be purged from the SP node 120 via the UAP node 110 to bypass a requirement for action by the service provider 12. As such, the user may not have to depend on service providers to purge the personal data.

Specifically, in response to a user request to revoke access of the service provider 12 to the personal data of the user, the UAP node 110 may update the access control information configured for the service provider 12 to revoke all access permissions of the service provider 12 (502). The UAP node 110 may update the meta data of the user with the updated access control information, for example, by adding the updated meta data to the meta data or replacing the original access control information configured for the service provider 12 with the updated access control information (504).

Then, the UAP node 110 may synchronize the updated meta data of the user to the SP node 120 via blockchain transactions (506). Similarly, the UAP node 110 may synchronized the updated meta data of the user to all other SP nodes whose corresponding service providers are serving the user and these SP nodes thus may store the updated meta data of the user.

Once the updated meta data of the user is synchronized to the SP node 120, it may trigger a purge of the personal data of the user stored on the SP node 120 (508). The SP node 120 may purge the personal data of the user by deleting an entire transaction chain of the user's personal data from the blockchain 123 on the SP node 120. For example, the transaction chain 126 stores transactions of the user's personal data, and thus the SP node 120 may delete the transaction chain 126. Because the transaction chain 126 is not linked with other transaction chains storing transactions for other users' personal data, deleting the transaction chain 126 may not tamper with the integrity/security of the other transaction chains in the blockchain 123. Additionally, to purge the user's personal data, the SP node 120 may further delete the state chain including historic states and current state of the user's personal data from the blockchain 123.

Figure 6:
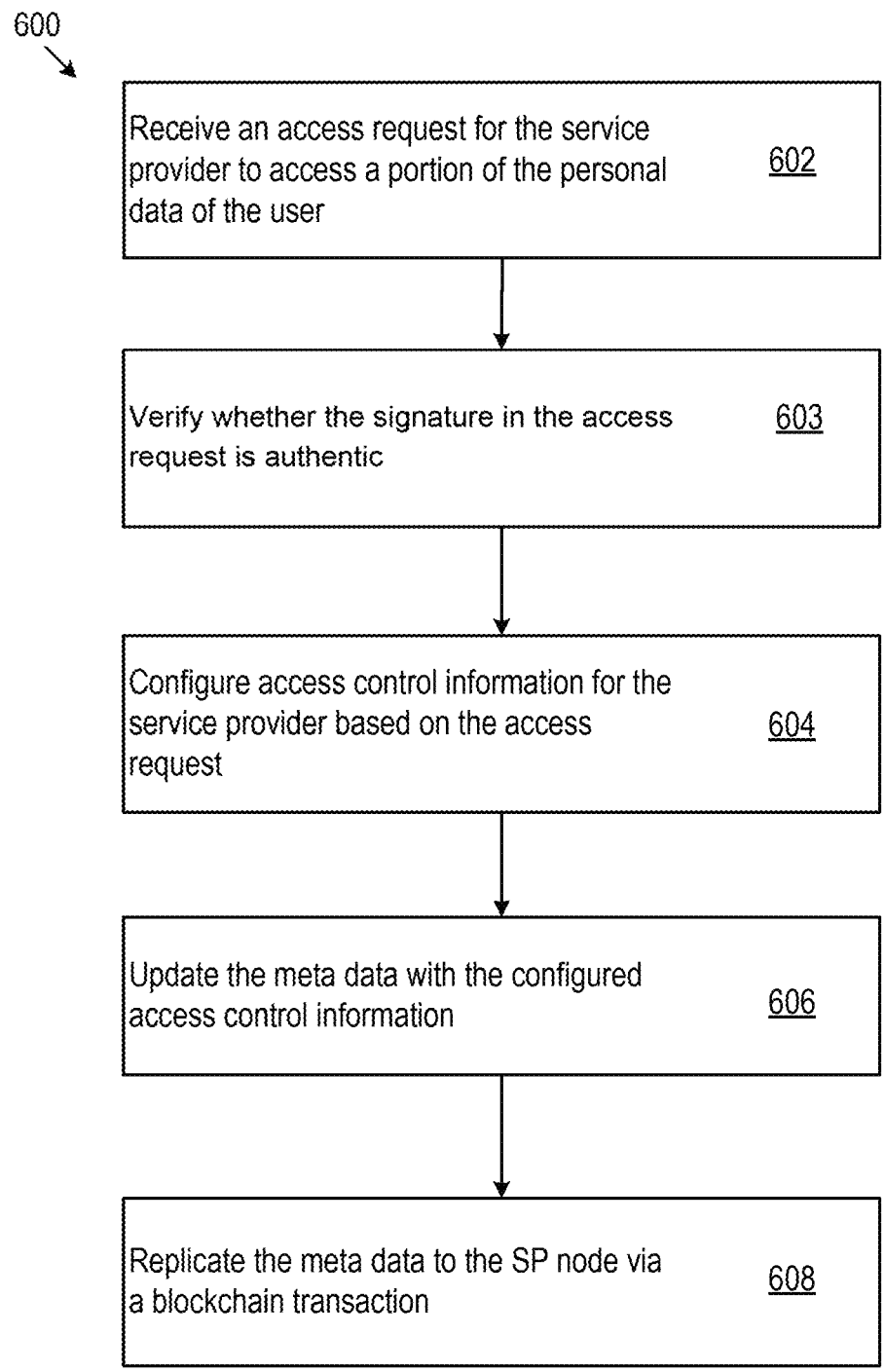
FIG. 6 illustrates an exemplary logic of a system.

FIG. 6 illustrates an exemplary management logic 600 that the system 100 may perform at the UAP node 110. Referring to FIGS. 1A, 1B and 6, the UAP node 110 may receive, from the SP node 120, an access request for the service provider 12 to access personal data of a user (602). The access request may include the user ID of the user, a signature signed with the private key of the user, and data types of the user's data records that the service provider 12 request to access.

Then, the UAP node 110 may verify if the signature of the user in the access request is authentic using the public key of the user (603). If the signature is authenticated, the UAP node 110 may continue to configure the access control information. Otherwise, the access request is not authorized by the user, and the UAP node 110 may disregard the access request.

When the signature is authenticated, the UAP node 110 may configure access control information for the service provider 12 to access the personal data of the user based on the access request (604). The access control information may include, for example, a create permission, a read permission, an update permission, and/or a delete permission. In some implementations, the system 100 may respectively configure the access control information for each of the data types that the service provider 12 request to access. Thus, data records belonging to different data types may be configured with different access control information. For example, the access control information configured for data records belonging to data type A includes a create permission, a read permission, and an update permission, while the access control information configured for data records belonging to a data type B includes read permission only.

Optionally, or in addition, prior to configuring the access control information, if the user is new to the UAP node 110, the UAP node 110 may generate the meta data of the user that includes the user ID and the public key of the user and may store the meta data on the transaction chain 114 of the UAP blockchain 113. The configured access control information may be added to the meta data of the user.

Subsequently, the UAP node 110 may update the meta data of the user with the configured access control information (606). The configured access control information may be added to the meta data stored on the transaction chain 114 of the UAP blockchain 113.

The UAP node 110 may replicate at least a portion of the meta data to the SP node 120 via blockchain transactions (608). For example, the replicated portion of the meta data may include the configured access control information for the service provider 12 to access the personal data of the user.

Figure 7:
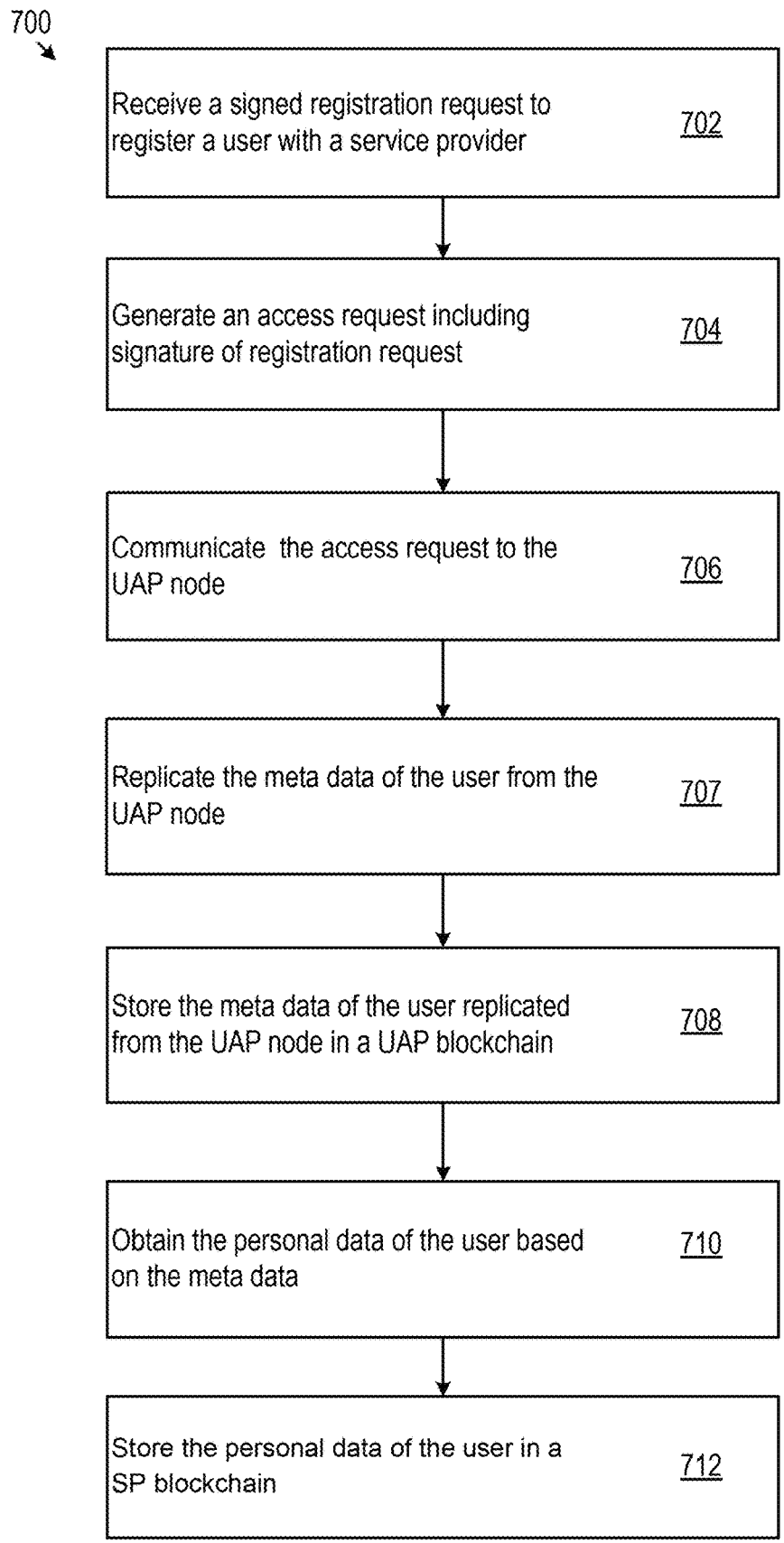
FIG. 7 illustrates an exemplary logic of a system.

FIG. 7 illustrates an exemplary management logic 700 that the system 100 may perform at the SP node 120. Referring to FIGS. 1A, 1B, and 7, the SP node 120 may receive a registration request to register a user with the service provider 12 associated with the SP node 120 (702). For example, the user device 11 may communicate the registration request to the SP node 120 via the client application 16 installed on the user device 11. The registration request may, for example, include the user ID of the user and signed with the private key of the user.

In order to provide services for the user, the service provider may request to access or manage the personal data of the user. Thus, upon receiving the registration request, the SP node 120 may generate an access request for the service provider 12 to access a personal data of the user (704). The access request may include, for example, the user ID of the user, the signature of the registration request signed with the private key of the user, and data types of the user's data records that the service provider 12 requested to access.

The SP node 120 may communicate the access request to the UAP node 110 (706). As discussed above with reference to FIG. 6, in response to the access request, the UAP node 110 may configure access control information for the service provider 12 and add the access control information to meta data of the user, which is stored on the transaction chain 114 of the UAP blockchain 113.

Then, the SP node 120 may replicate the meta data of the user from the UAP node 110 via a blockchain transaction (707) and store the replicated meta data on the transaction chain 124 of the SP blockchain 123 (708). In this way, the replication or synchronization of the meta data between the UAP node 110 and the SP node 120 may be achieved via blockchain transactions.

Once the service provider 12 has access permission to the personal data of the user, the SP node 120 may obtain the personal data of the user based on the meta data of the user stored on the SP node (710). For example, the meta data includes data types of the data records to which the service provider 12 is granted access permission. In an example, the SP node 120 may replicate these data records per data type from other SP nodes of the blockchain network 19 via blockchain transactions if other SP nodes have access to data records of the user with the same data type. For example, the SP node 120 may replicate data records of the user belonging to data type A from a first SP node while replicating data records of the user belonging to data type B from a second SP node.

Then, the SP node 120 may store the personal data of the user including all the replicated data records on the transaction chain 126 of the SP blockchain 123 on the SP node 120 such that the replication or synchronization of the personal data of the user between the SP nodes may be achieved via blockchain transactions (712).

FIG. 8 shows an example execution environment 800 for the system 100 for managing user personal data as described herein. The execution environment 800 may be hardware and/or a combination of hardware and software that includes system logic 814 to support execution of the management logic 600 or 700 described above. The system logic 814 may include processors 816, memory 820, and/or other circuitry. In various implementations, the execution environment 800 may act as dedicated circuitry that is configured to implement the management logic 600 or 700.

The memory 820 may include blockchain blocks 852, hash parameters 854, and network data 856 to support blockchain manipulation, including reading and writing. The memory 820 may further include applications and structures 866, for example, cryptographic primitives, security credentials, machine instructions, templates, or other structures to support access permission configurations, signature authentication, data replication/synchronization, data purging, blockchain read/writes or other tasks described herein. The applications and hardware may implement the management logic 600 and/or 700.

The execution environment 800 may also include one or more communication interfaces 812, which may support wireless, e.g. Bluetooth, Wi-Fi, WLAN, cellular (4G, LTE/A, 5G), and/or wired, Ethernet, Gigabit Ethernet, optical networking protocols. The communication interfaces 812 may also include serial interfaces, such as universal serial bus (USB), serial ATA, IEEE 1394, lighting port, I$^2$C, slimBus, or other serial interfaces. The communication interfaces 812 may support and/or implement data replication/synchronization, blockchain network participation or other tasks. The execution environment 800 may include power units 825 and various input interfaces 828. The execution environment may also include a user interface 818 that may include human-to-machine interface devices and/or graphical user interfaces (GUI). The user interface 818 may be used to support and/or implement local or localized operation of the execution environment 800. In various implementations, the execution environment 800 may be distributed over one or more physical servers, be implemented as one or more virtual machines, be implemented in container environments such as Cloud Foundry or Docker, and/or be implemented in Serverless (functions as-a-Service or virtual machine) environments.

In some cases, the execution environment 800 may be a specially defined computational system deployed in a cloud platform. In some cases, the parameters defining the execution environment may be specified in a manifest for cloud deployment. The manifest may be used by an operator to requisition cloud-based hardware resources, and then deploy the software components, for example, the applications and structures 866, of the execution environment onto the hardware resources. In some cases, a manifest may be stored as a preference file such as a YAML (yet another mark-up language), JSON, or other preference file type.

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, in hardware, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

The techniques and architectures are discussed above in the context that the user may represent individuals. However, it should be appreciated that the discussed techniques and architectures may also be applicable to the user representing a group of individuals, such as a family, a sports team, etc., as well as an entity, such as a corporation, school, organization, etc.

Throughout the specification and claims, terms may have nuanced meanings suggested or implied in context beyond an explicitly stated meaning. Likewise, the phrase "in one embodiment/implementation" as used herein does not necessarily refer to the same embodiment and the phrase "in another embodiment/implementation" as used herein does not necessarily refer to a different embodiment. It is intended, for example, that claimed subject matter includes combinations of example embodiments in whole or in part.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

In general, terminology may be understood at least in part from usage in context. For example, terms, such as "and", "or", or "and/or," as used herein may include a variety of meanings that may depend at least in part on the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Reference throughout this specification to features, advantages, or similar language does not imply that all of the features and advantages that may be realized with the present solution should be or are included in any single implementation thereof. Rather, language referring to the features and advantages is understood to mean that a specific feature, advantage, or characteristic described in connection with an embodiment is included in at least one embodiment of the present solution. Thus, discussions of the features and advantages, and similar language, throughout the specification may, but do not necessarily, refer to the same embodiment.

Furthermore, the described features, advantages and characteristics of the present solution may be combined in any suitable manner in one or more embodiments. One of ordinary skill in the relevant art will recognize, in light of the description herein, that the present solution can be practiced without one or more of the specific features or advantages of a particular embodiment. In other instances, additional features and advantages may be recognized in certain embodiments that may not be present in all embodiments of the present solution.

While various embodiments have been described, it will be apparent to those of ordinary skill in the art that many more embodiments and implementations are possible. Accordingly, the embodiments described herein are examples, not the only possible embodiments and implementations.

What is claimed is:

1. A system comprising:
    a user access provider (UAP) node in communication with a service provider (SP) node associated with a service provider using a network,
    wherein:
       the SP node comprises a SP blockchain storing personal data of users on a plurality of separate SP transaction chains,
          the plurality of SP transaction chains comprising a first SP transaction chain storing transactions for a first personal data of a first user, and a second SP transaction chain storing transactions for a second personal data of a second user,
       the UAP node comprising:
          a UAP blockchain storing a meta data of the user on a UAP transaction chain, the meta data comprising access control information for the service provider, and the access control information configured to control access by authorized SP nodes to personal data of the users; and
          a processor configured to:
             receive, from the SP node, an access request for the service provider to access a portion of the personal data of the first user,
             configure access control information for controlling access, by the service provider, to a portion of the personal data of the first user based on the access request,
             update the meta data with the configured access control information, and
             providing the meta data with the access control information to the SP node, wherein the SP node obtains at least the portion of the meta data to the SP node via a blockchain transaction based on the access control information by identifying data types for which the service provider has access permission and replicating data records associated with the identified data type from another SP node having access to data records of the identified data type for the user, wherein at least the portion of the personal data of the user is stored on an SP transaction chain of the SP blockchain.

2. The system of claim 1, wherein the UAP node is prevented from accessing the personal data of the user.

3. The system of claim 1, wherein the personal data comprises a plurality of data records,
    the data records categorized into respective data types,
    the data types indicating categorizations of content in the data records,
    wherein, the access request comprises data types that the service provider requests to access,
    and wherein the processor of the UAP node is configured to:
       for each of the data types that the service provider requests to access, respectively configure the access control information for the service provider to access data records belonging to the data type.

4. The system of claim 3, wherein the processor of the UAP node is further configured to:
    create a custom permission record listing a plurality of service providers that have access to a specific data record in the personal data; and
    store the custom permission record on the UAP transaction chain.

5. The system of claim 1, wherein, the access request comprises a user identifier of the user and a signature signed with a private key of the user, and the processor of the UAP node is further configured to:
    verify whether the signature is authentic via a public key of the user pairing with the private key of the user; and
    in response to the signature being authentic, configure the access control information based on the access request.

6. The system of claim 5, wherein the processor of the UAP node is configured to:
    in response to the user being a new user to the UAP node, prior to configuring the access control information, generate the meta data of the user with the user identifier and the public key.

7. The system of claim 1, wherein the access control information comprises at least one of a create permission, a read permission, an update permission, or a delete permission.

8. The system of claim 1, wherein the processor of the UAP node is further configured to:
receive, from a user device, a user registration request to register the user,
wherein the user registration request comprises a public key of the user;
add the public key to the meta data of the user; and
generate a user identifier for the user in response to the user registration request.

9. The system of claim 1, wherein the processor of the UAP node is further configured to, in response to a user request to revoke access of the service provider to the personal data of the user,
update the access control information configured for the service provider to revoke access permission of the service provider;
update the meta data with the updated access control information; and
synchronize the updated meta data to the SP node to trigger purging of the personal data of the user stored on the SP transaction chain of the SP node.

10. The system of claim 9, wherein the processor of the UAP node is further configured to:
synchronize, via the blockchain transaction, the updated meta data to other SP nodes storing the meta data of the user.

11. A system comprising:
a service provider (SP) node in communication with a user access provider (UAP) node using a blockchain network,
the SP node comprising a SP blockchain comprising a plurality of separate SP transaction chains,
the plurality of separate SP transactions comprising a first SP transaction chain storing transactions for a first user, and a second SP transaction chain storing transactions for a second user, and
the SP node comprising a processor configured to:
receive a registration request,
the registration request to register a user with a service provider associated with the SP node;
generate an access request for the service provider,
the access request to access a portion of personal data of the user based on the registration request;
communicate the access request to the UAP node,
receive, from the UAP node, access control information configured to control access to the personal data of the user by the service provider,
the access control information configured by the UAP node response to the access request by adding the access control information to meta data of the user,
the UAP node comprising a UAP blockchain storing the meta data on a UAP transaction chain;
replicate the meta data of the user from the UAP node via a blockchain transaction;
store the meta data of the user on a third SP transaction chain of the SP blockchain;
obtain the portion of the personal data of the user based on the meta data stored on the SP node using on the access control information,
the portion of the personal data of the user is obtained based on the meta data by:
identifying data types for which the service provider has access permission based on the access control information; and
replicating data records belonging to each of the identified data types, respectively, from another SP node of the blockchain network, wherein the another SP node has access to data records of the data type; and
store the portion of the personal data of the user on a fourth SP transaction chain of the SP blockchain.

12. The system of claim 11, wherein the SP node is prevented from modifying the meta data stored on the SP node.

13. The system of claim 11, wherein the personal data comprises a plurality of data records which are categorized into respective data types indicating categorizations of content in each data record of the plurality of data records, and the meta data comprises a user identifier of the user.

14. The system of claim 13, the processor of the SP node is further configured to:
receive, from a user device, an update request to update a data record in the personal data of the user;
communicate a confirmation request to the user device, wherein the confirmation request is signed with a private key of the user, by the user device, to generate a signature of the confirmation request;
receive the signature from the user device;
determine whether the signature is authentic via a public key of the user pairing with the private key of the user; and
in response to the signature being authentic, update the data record to the personal data of the user stored on the SP node.

15. The system of claim 14, wherein the SP node is further configured to:
determine if updating the data record requires a signature of the user based on a data type of the data record; and
communicate the confirmation request to the user device in response to the signature of the user being required.

16. The system of claim 14, the processor of the SP node is further configured to:
in response to the signature being authentic, synchronize the updated data record to other SP nodes of the blockchain network that have access to data records belonging to a same data type with the updated data record.

17. The system of claim 13, further comprising a custodian service provider node included in the blockchain network in communication with the SP node, wherein the custodian service provider node is not associated with the service provider and includes a processor configured to:
store as a backup, for each data type, the personal data of the user on a custodian SP transaction chain of the custodian service provider node,
wherein the processor of the SP node is configured to obtain the portion of the personal data of the user based on the meta data by:
Identification of data types to which the service provider has access permission based on the meta data; and
for each of the identified data types, respectively replicate data records belonging to the data type from the custodian service provider node via blockchain transactions.

18. The system of claim 11, wherein the processor of the SP node is further configured to:

in response to the meta data of the user being updated to indicate revocation of access permission of the service provider to the personal data of the user, purge the personal data of the user by deleting the fourth SP transaction chain storing transactions for the personal data of the user from the SP blockchain.

19. A method comprising:

receiving, at a user access provider (UAP) node from a service provider (SP) node, an access request for the service provider to access a portion of personal data of a user, wherein the UAP node is in communication with the SP node via a network, the SP node comprising an SP blockchain storing personal data of users on a plurality of separate SP transaction chains including a first SP transaction chain storing transactions corresponding to first personal data of the user and a second SP transaction chain storing transactions corresponding to second personal data of a second user, the personal data stored at each SP transaction chain of the plurality of SP transaction chains categorized into respective data types indicating categorizations of content included in the personal data, the UAP node comprising a UAP blockchain, the UAP blockchain storing a meta data of the user at a UAP transaction chain, the meta data comprising access control information for the service provider, and the access control information configured to control access by authorized SP nodes to personal data of users;

the access request comprising a data type corresponding to a category of content that the service provider requests to access;

configuring access control information for the service provider to access at least a portion of the personal data of the user based on the data type identified in the access request;

updating the meta data with the configured access control information; and providing the meta data with the access control information to the SP node, wherein the SP node obtains at least the portion of the personal data of the user via a blockchain transaction based on the access control information by identifying data types for which the service provider has access permission and replicating data records associated with the identified data type from another SP node having access to data records of the identified data type for the user, wherein at least the portion of the personal data of the user is stored on an SP transaction chain of the SP blockchain.

* * * * *

UNITED STATES PATENT AND TRADEMARK OFFICE
CERTIFICATE OF CORRECTION

PATENT NO. : 11,436,368 B2
APPLICATION NO. : 16/837746
DATED : September 6, 2022
INVENTOR(S) : Tal Beno et al.

It is certified that error appears in the above-identified patent and that said Letters Patent is hereby corrected as shown below:

In the Claims

At Column 17, Claim number 11, Line number 54, delete "UAP node response" and replace with --UAP node in response--.

Signed and Sealed this
First Day of November, 2022

Katherine Kelly Vidal
*Director of the United States Patent and Trademark Office*